United States Patent
Moreno

(10) Patent No.: US 9,708,283 B2
(45) Date of Patent: *Jul. 18, 2017

(54) ISOFLAVONOID COMPOSITIONS AND METHODS FOR THE TREATMENT OF CANCER

(75) Inventor: Ofir Moreno, Poway, CA (US)

(73) Assignee: MEI PHARMA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/881,599

(22) PCT Filed: Nov. 1, 2011

(86) PCT No.: PCT/US2011/058820
§ 371 (c)(1),
(2), (4) Date: Jun. 13, 2013

(87) PCT Pub. No.: WO2012/061413
PCT Pub. Date: May 10, 2012

(65) Prior Publication Data
US 2013/0273177 A1    Oct. 17, 2013

Related U.S. Application Data

(60) Provisional application No. 61/408,972, filed on Nov. 1, 2010.

(51) Int. Cl.
| | |
|---|---|
| C07D 311/58 | (2006.01) |
| A61K 31/353 | (2006.01) |
| A61K 47/40 | (2006.01) |
| A61P 35/00 | (2006.01) |
| A61K 31/337 | (2006.01) |
| A61K 31/555 | (2006.01) |
| A61K 33/24 | (2006.01) |
| A61K 45/06 | (2006.01) |
| A61K 9/00 | (2006.01) |
| A61K 9/51 | (2006.01) |

(52) U.S. Cl.
CPC .......... *C07D 311/58* (2013.01); *A61K 9/0019* (2013.01); *A61K 9/5161* (2013.01); *A61K 31/337* (2013.01); *A61K 31/353* (2013.01); *A61K 31/555* (2013.01); *A61K 33/24* (2013.01); *A61K 45/06* (2013.01); *A61K 47/40* (2013.01)

(58) Field of Classification Search
CPC .... C07D 311/58; A61K 31/353; A61K 47/40; A61K 9/5161
USPC .......................................... 514/456; 549/406
See application file for complete search history.

(56) References Cited

U.S. PATENT DOCUMENTS

| | | |
|---|---|---|
| 3,340,276 A | 9/1967 | Carney |
| 3,471,520 A | 10/1969 | Irmscher et al. |
| 3,535,344 A | 10/1970 | Irmscher |
| 4,157,984 A | 6/1979 | Zilliken |
| 4,218,489 A | 8/1980 | Zilliken |
| 4,232,122 A | 11/1980 | Zilliken |
| 4,234,577 A | 11/1980 | Zilliken |
| 4,366,082 A | 12/1982 | Zilliken |
| 4,366,248 A | 12/1982 | Zilliken |
| 4,368,264 A | 1/1983 | Zilliken |
| 4,390,559 A | 6/1983 | Zilliken |
| 4,447,622 A | 5/1984 | Salman et al. |
| 4,644,012 A | 2/1987 | Tsuda et al. |
| 4,814,346 A | 3/1989 | Albert et al. |
| 5,024,998 A | 6/1991 | Bodor |
| 5,059,609 A | 10/1991 | Eggler et al. |
| 5,134,127 A | 7/1992 | Stella et al. |
| 5,280,040 A | 1/1994 | Labroo et al. |
| 5,376,645 A | 12/1994 | Stella et al. |
| 5,389,646 A | 2/1995 | Labroo |
| 5,464,862 A | 11/1995 | Labroo et al. |
| 5,696,149 A | 12/1997 | Korsgaard et al. |
| 5,726,202 A | 3/1998 | Shalmi et al. |
| 5,756,539 A | 5/1998 | Skrumsager et al. |
| 5,780,503 A | 7/1998 | Biftu et al. |
| 5,849,461 A | 12/1998 | Hatakeyama et al. |
| 5,874,418 A | 2/1999 | Stella et al. |
| 5,883,118 A | 3/1999 | Shalmi et al. |
| 5,919,817 A | 7/1999 | Jacobsen et al. |
| 5,958,967 A | 9/1999 | Jacobsen et al. |
| 5,985,306 A | 11/1999 | Jacobsen et al. |
| 5,994,390 A | 11/1999 | Jacobsen et al. |
| 5,998,451 A | 12/1999 | Eggler et al. |
| 6,005,003 A | 12/1999 | Nique |
| 6,043,269 A | 3/2000 | Jacobsen et al. |

(Continued)

FOREIGN PATENT DOCUMENTS

| | | |
|---|---|---|
| CA | 2581316 | 3/2006 |
| EP | 0267155 | 10/1987 |

(Continued)

OTHER PUBLICATIONS

U.S. Appl. No. 60/611,299, filed Sep. 21, 2004, Heaton.
Abegaz, et al., Isoflavonoids from the roots of Salsola somalensis. Phytochemistry. 1991; 30(4):1281-4 (Abstract Only in English).
Agarwal, et al., Isoflavones of two Iris species. Phytochemistry (Elsevier) 1984; 23(11):2703-4 (Abstract Only in English).
Agarwal, et al., Phenolic constituents of Iris Milesii rhizomes, Phytochemistry (Elsevier) 1984; 23(6):1342-3 (Abstract Only in English).
Aggarwal, et al., From chemoprevention to chemotherapy: common targets and common goals. Expert Opin. Investig. Drugs. 2004;13(10):1327-38.

(Continued)

*Primary Examiner* — Irina Neagu
(74) *Attorney, Agent, or Firm* — Wilson Sonsini Goodrich & Rosati

(57) ABSTRACT

Provided herein is a pharmaceutical composition comprising an isoflavonoid derivative and a cyclodextrin. Also provided herein are methods of treating cancer, sensitizing cancer cells, and inducing apoptosis in cancer cells by administering such compositions. In specific instances, provided herein are intravenous compositions and therapies.

11 Claims, No Drawings

(56) References Cited

U.S. PATENT DOCUMENTS

| | | | |
|---|---|---|---|
| 6,316,494 B1 | 11/2001 | Jacobsen et al. | |
| 6,479,467 B1 | 11/2002 | Buchanan et al. | |
| 6,509,323 B1 | 1/2003 | Davis et al. | |
| 6,610,671 B2 | 8/2003 | Buchanan et al. | |
| 6,610,733 B2 | 8/2003 | Park et al. | |
| 6,645,951 B1 | 11/2003 | Jo et al. | |
| 6,649,648 B1 | 11/2003 | Kelly et al. | |
| 6,660,804 B1 | 12/2003 | Weltrowski et al. | |
| 7,056,952 B1 | 6/2006 | Joannon | |
| 7,202,273 B2 | 4/2007 | Kelly et al. | |
| 7,601,855 B2 | 10/2009 | Heaton | |
| 8,080,675 B2* | 12/2011 | Heaton et al. | 549/399 |
| 8,084,628 B2* | 12/2011 | Heaton et al. | 549/403 |
| 8,163,795 B2* | 4/2012 | Heaton et al. | 514/457 |
| 8,461,361 B2* | 6/2013 | Heaton et al. | 549/399 |
| 8,697,891 B2* | 4/2014 | Heaton et al. | 549/403 |
| 8,957,109 B2 | 2/2015 | Heaton et al. | |
| 9,198,895 B2 | 12/2015 | Heaton et al. | |
| 9,381,186 B2 | 7/2016 | Heaton et al. | |
| 2002/0128468 A1 | 9/2002 | Buchanan et al. | |
| 2004/0063663 A1 | 4/2004 | Buchanan et al. | |
| 2004/0106575 A1 | 6/2004 | Zhang et al. | |
| 2004/0109888 A1 | 6/2004 | Pun et al. | |
| 2006/0074126 A1* | 4/2006 | Heaton et al. | 514/456 |
| 2006/0074127 A1 | 4/2006 | Heaton et al. | |
| 2006/0167037 A1 | 7/2006 | Kelly et al. | |
| 2006/0183728 A1 | 8/2006 | Kelly et al. | |
| 2007/0155695 A1 | 7/2007 | Wirth et al. | |
| 2008/0069900 A1 | 3/2008 | Kelly et al. | |
| 2009/0317490 A1 | 12/2009 | Heaton et al. | |
| 2010/0130598 A1 | 5/2010 | Brown et al. | |
| 2010/0152284 A1 | 6/2010 | Brown et al. | |
| 2010/0173983 A1 | 7/2010 | Brown et al. | |
| 2012/0004296 A1 | 1/2012 | Heaton et al. | |
| 2012/0039917 A1 | 2/2012 | Husband et al. | |
| 2012/0114766 A1 | 5/2012 | Heaton et al. | |
| 2012/0172424 A1 | 7/2012 | Heaton et al. | |
| 2012/0251630 A1 | 10/2012 | Alvero et al. | |
| 2014/0161908 A1 | 6/2014 | Heaton et al. | |
| 2014/0170243 A1 | 6/2014 | Heaton et al. | |
| 2014/0234295 A1* | 8/2014 | Jeoffreys et al. | 424/133.1 |
| 2015/0238458 A1 | 8/2015 | Heaton et al. | |
| 2015/0352074 A1 | 12/2015 | Heaton et al. | |
| 2016/0136129 A1 | 5/2016 | Heaton et al. | |
| 2016/0287555 A1 | 10/2016 | Heaton et al. | |

FOREIGN PATENT DOCUMENTS

| | | |
|---|---|---|
| EP | 0313295 | 4/1989 |
| EP | 0470310 | 12/1992 |
| EP | 0955286 | 11/1999 |
| GB | 1433013 | 4/1976 |
| JP | 2000-506507 | 5/2000 |
| JP | 2001-502706 | 2/2001 |
| JP | 2001-502711 | 2/2001 |
| JP | 2006096734 A | 4/2006 |
| JP | 2012144537 A | 8/2012 |
| JP | 2014237638 A | 12/2014 |
| WO | WO-80/02098 A1 | 10/1980 |
| WO | WO-94/08986 A1 | 4/1994 |
| WO | WO-94/20099 A1 | 9/1994 |
| WO | WO-96/21442 A1 | 7/1996 |
| WO | WO-96/21443 A1 | 7/1996 |
| WO | WO-96/21444 A1 | 7/1996 |
| WO | WO-96/22091 A1 | 7/1996 |
| WO | WO-96/22092 A1 | 7/1996 |
| WO | WO-96/22093 A1 | 7/1996 |
| WO | WO-97/25035 A1 | 7/1997 |
| WO | WO-97/25036 A1 | 7/1997 |
| WO | WO-97/25037 | 7/1997 |
| WO | WO-97/25038 A1 | 7/1997 |
| WO | WO-98/02154 A1 | 1/1998 |
| WO | WO-98/02156 A1 | 1/1998 |
| WO | WO-98/08503 A1 | 3/1998 |
| WO | WO-98/17662 A1 | 4/1998 |
| WO | WO-98/18770 A1 | 5/1998 |
| WO | WO-98/18771 A1 | 5/1998 |
| WO | WO-98/18772 A1 | 5/1998 |
| WO | WO-98/18773 A1 | 5/1998 |
| WO | WO-98/18774 A1 | 5/1998 |
| WO | WO-98/18775 A1 | 5/1998 |
| WO | WO-98/18776 A1 | 5/1998 |
| WO | WO-98/18778 A1 | 5/1998 |
| WO | WO-98/18779 A1 | 5/1998 |
| WO | WO-98/25916 A1 | 6/1998 |
| WO | WO-98/32437 A1 | 7/1998 |
| WO | WO-98/33499 A1 | 8/1998 |
| WO | WO-98/33500 A1 | 8/1998 |
| WO | WO-99/49862 A1 | 10/1999 |
| WO | WO-99/55898 A1 | 11/1999 |
| WO | WO-99/63974 A2 | 12/1999 |
| WO | WO-99/65893 A1 | 12/1999 |
| WO | WO-00/49009 | 8/2000 |
| WO | WO-00/66576 A1 | 11/2000 |
| WO | WO-01/17986 A1 | 3/2001 |
| WO | WO-01/26651 A2 | 4/2001 |
| WO | WO-01/54699 A1 | 8/2001 |
| WO | WO-02/02548 A1 | 1/2002 |
| WO | WO-02/059113 A1 | 8/2002 |
| WO | WO-03/016270 A2 | 2/2003 |
| WO | WO-03/035635 A1 | 5/2003 |
| WO | WO-03/063859 A1 | 8/2003 |
| WO | WO-03/086386 A1 | 10/2003 |
| WO | WO-2004/030662 A1 | 4/2004 |
| WO | WO-2005/049008 A1 | 6/2005 |
| WO | WO-2006/032085 A1 | 3/2006 |
| WO | WO-2006/032086 A1 | 3/2006 |
| WO | WO-2008/052256 | 5/2008 |
| WO | WO-2008/113100 | 9/2008 |
| WO | WO-2010/022467 | 3/2010 |
| WO | WO-2010/045674 | 4/2010 |
| WO | WO-2012/061409 | 5/2012 |
| WO | WO-2012/061413 | 5/2012 |

OTHER PUBLICATIONS

Akimoto, et al., Genistein, a tyrosine kinase inhibitor, enhanced radiosensitivity in human esophageal cancer cell lines in vitro: possible involvement of inhibition of survival signal transduction pathways. Int. J. Radiation Oncology Biol. Phys. 2001; 50(1):195-201.

Antus, et al., Synthesis of some pterocarpenes obtained from Brya ebenus, J. Chem. Soc., Perkin Trans. 1982;6:1389-94 (Abstract Only in English).

Arnone, et al., Isoflavonoid constituents of the West African red wood, Baphia nitida. Phtyochemistry. 1981; 20(4):799-801 (Abstract Only in English).

Bellisarii, et al., Tumor necrosis factor-α and cardiovascular diseases. Ital Heart J. 2001;2(6):408-17.

Berge, et al., Pharmaceutical Salts. J Pharamaceutical Sciences, 66(1):1-19 (1977).

Bezuidenhoudt et al., Synthesis of Isoflavanoid Oligomers Using a Pterocarpan as Inceptive Electrophile. J Chem Soc Parkin Trans. 1984; 1:2767-78.

Bradbury, Some oestrogenic 4-phenyl-substituted isoflav-3-ENS, Aust J Chem. 1953;6:447-49.

Briviba, et al., Isoflavonoids as inhibitors of lipid peroxidation and quenchers of singlet oxygen. Antioxidants in Health and Disease, 7(Flavonoids in Health and Disease). 1998:295-302 (Abstract Only in English).

Bury, et al., Synthesis and pharmacological evaluation of novel cis-3,4-diaryl-hydroxychromanes as high affinity partial agonists for the estrogen receptor. Bioorg Med Chem. 2002;10:125-145.

Caltagirone, et al., Flavanoids apigenin and quercetin inhibit melanoma growth and metastatic potential. Int J Cancer Suppl. 2002; 87(4):595-600 (Abstract Only in English).

Caltagirone, et al., Interaction with type II estrogen binding sites and antiproliferative activity of tamoxifen and quercetin in human non-small-cell lung cancer, American Journal of Respiratory Cell and Molecular Biology. Jul. 1997; 17:(1):51-9 (Abstract Only in English).

(56) References Cited

OTHER PUBLICATIONS

Challa et al., Cyclodestrins in drug delivery: An Updated Review. AAPS PharmSciTech 6(2): Article 43, E329-E357 (2005).
Constantinou, et al. Phenoxodiol (2H-1-Benzopyran-7-0, 1, 3-(4-hydroxyphenyl), a Novel Isoflavone Derivative, Inhibits DNA Topoisomerase II by Stabilizing the Cleavable Complex. Anticancer Research. 2002;22:2581-86.
Constantinou, et al., Phenoxodiol, a novel isofavone derivative, inhibits dimethylbenz[a]anthracene(DMBA)-induced mammary carcinogenesis in female Sprague—Dawley rats. Eur J Cancer. 2003; 39:1012-18.
De Vincenzo, et al.,Flavanoids and negative control of cell proliferation in ovarian tumors. Acta Medica Romana. 1992; 30(1-2):126-32 (Abstract Only in English).
Dorai, et al , Role of chemopreventive agents in cancer therapy. Cancer Lett. 2004; 215:129-40.
EP 05779877.9 Search Report dated Apr. 28, 2009.
EP 05787045.3 Search Report dated Oct. 7, 2008.
EP 11180383.9 Office Action dated Mar. 25, 2014.
Fukui, et al., The synthesis of irisolone. Bull. Chem. Soc. Japan. 1965; 38(6):887-93 (Abstract Only in English).
Gamble, et al., Phenoxodiol, an experimental anticancer drug, shows potent antiangiogenic properties in addition to its antitumour effects. Int. J. Cancer. 2006; 118:2412-20.
Giacomelli. et al., Silybin and its bioavailable, phospholipid complex(IdB1016) potentiate in vitro and in vivo the activity of cisplatin. Life Sciences. Feb. 8, 2002; 70(12):1447-59 (Abstract Only in English).
Gupta et al., The use of Friedel-Crafts reactions for the synthesis of deoxybenzoins. Indian J Chem. 1968; 6(9):481-4 (Abstract Only in English).
Hem Chandra Jha, et al., Carbon -13- chemical shift assignments of chromones and isoflavones. Can J Chem. 1980; 58:1211-19.
Hersey, et al., How melanoma cells evade trail-induced apoptosis. Nat Rev Cancer. Nov. 2001; 1(2)142-50.
Horie, et al., Studies of the selective O-alkylation and dealkylation of flavonoids. XX. A convenient method for synthesizing 5,6,7-trihydroxyisoflavones and 5,6-dihydroxy-7-methoxyisoflavones. Pharm Bull. 1996; 44(3):486-91 (Abstract Only in English).
Hu et al., Identification of CYP1A2 as the main isoform for the Phase 1 hydroxylated metabolism of genistein and a prodrug converting exzyme of methylated isoflavones. Drug Metabolism and Dispostion, 31(7):924-931 (2003).
Ito, et al., Isoflavonoids from Belamcanda chinensis. Pharm Bull. 2001; 49(9):1229-31 (Abstract Only in English).
Kakeji, et al., Preclinical studies of the combination of angiogenic inhibitors with cytotoxic agents. Invest New Drugs. 1997; 15:39-48.
Kamsteeg, et al., Phenoxodiol—an isoflavone analog—induces apoptosis in chemoresistant ovarian cancer cells. Oncogene. 2003; 22:2611-20.
Kang, et al., "Scientific Analysis of Formulation Theory of Chungpesagan-tang; In vitro Cytotoxicity of Cisplatin Combined with Chungpesagan-tang", Natural Product Sciences, vol. 6(4), pp. 165-169, (2000).
Kanzawa, et al., Evaluation of synergism by a novel three-dimensional model for the combined action of cisplatin and etoposide on the growth of a human small-cell lung-cancer cell line, SBC-3. Int. J. Cancer 71, 311-319 (1997).
Khoshyomn, et al., Synergistic Action of Genistein and Ciplatin on Growth Inhibition and Cytotoxicity of Human Medulloblastoma Cells. Pediatr Neurosurg. 2000; 33:123-31.
Kinjo, et al., Novel santalin analogs from Pterpcarpus santalinus (leguminosae): their biogenesis and anti-oxidative activities. Tennen Yuki Kagobutsu Toronkai Koen Yoshishu. 1995; 37:493-8 (Abstract Only in English).
Klus, et al., Formation of polyhydroxylated isoflavones from the soybean seed isoflavones daidzein and glycitein by bacteria isolated from tempe. Arch Microbiol. 1995; 164(6):428-34 (Abstract Only in English).

Kothari, et al., Inhibition of cholesterol ester trnasfer protein by CGS 25159 and changes in lipoproteins in hamsters: Atherosclerosis. (Shannon, Ireland) 1997; 128(1):59-66.
Kulling, et al., Oxidative metabolism of the soy isoflavones daidzein and genistein in humans in vitro and in vivo. J Agric Food Chem. 2001; 49(6):3024-33 (Abstract Only in English).
Lawson, Estrogenic activity of some derivatives of isoflaven and isoflavanol. J Chem Soc. 1954:4448-50 (Abstract Only in English).
Lei, et al., Enhancement of Chemosensitivity and Programmed Cell death by Tyrosine Kinase Inhibitors Correlates with EGFR Expression in Non-Small Cell Lung Cancer Cells. Anticancer Res. 1989; 19:221-28.
Li, et al., Apoptosis-Inducing Effect of Chemotherapeutic Agents Is Potentiated by Soy Isoflavone Genistein, a Natural Inhibitor of NF-KB in BxPC-3 Pancreatic Cancer Cell Line. Pancreas. 2004; (28)4:e90-5.
Mani, et al, Isoflavones. III. Nitration of 7,8- and 6,7-dihydroxyisoflavones and their methyl ether. J Inst Chem. 1971; 43(6):234-40 (Abstract Only in English).
Mani, et al., Isoflavones. I. Bromination of isoflavones. J Inst Chem. 1974; 46(Pt.3):61-5 (Abstract Only in English).
Mansour, et al., Enhancement of Chemotherapeutic Efficacy by Combining Agents that Block IL-10 in CLL Cell Lines. New Jersey Medical School, UMDNJ, Newark, NJ, USA Blood. Nov. 16, 2002; 100(11) Abstract No. 4997. Print (Abstract Only in English).
McDonnell, et al., Improvement in Efficacy of Chemoradiotherapy by Addition of and Antiangiogenic Agent in a Murine Tumor Model. J Surg Res. 2004; 116:19-23.
Micheli, et al., Coumestro, Plant Phenolics, and Synthetic Estrogens: a Correlation of Structure and Activity, Journal of Medicinal and Pharmaceutical Chemistry, vol. 5, 1962, pp. 321-335.
Montandon, et al., In-vitro versus in-vivo activities of new 5-lipoxygenase inhibitors with anti-inflammatory activity, Int J Tissue React. 1989; 11(3); 107-12 (Abstract Only in English).
Nakata et al., C225 Antiepidermal Growth Factor Receptor Antibody Enhances the Efficacy of Docetaxel Chemoradiotherapy. Int J Radiation Oncology Biol Phys. 2004; 59(4): 1163-73.
Neelam, et al., Combination of flavone acetic acid (FAA) with adriamycin, cis-platinum and difloouoromethylornithine (DFMO) in vitro against human colon cancer cells. Invest New Drugs. Aug. 1990; 8(3):263-8 (Abstract Only in English).
O'Dwyer, et al., Antitumor Activity and Biochemical Effects of Aphidicolin Glycinate(NSC 303812) Alone and in Combination with Cisplatin in Vivo. Cancer Res. Feb. 1, 1994; 54:724-29.
O'Neill, et al., Inducible Isoflavonoids from the Lima Bean, Phaseolus Lunatus. Phytochemistry. 1986; 25(6): 1315-22.
PCT/AU2005/01435 ISR dated Dec. 21, 2005.
PCT/AU2004/001619 ISR dated Feb. 2, 2005.
PCT/AU2005/001436 ISR dated Dec. 21, 2005.
PCT/US2011/058815 International Report on Patentability dated May 7, 2013.
PCT/US2011/058815 International Search Report and Written Opinion dated Mar. 12, 2012.
PCT/US2011/058820 International Preliminary Report on Patentability dated May 8, 2013.
PCT/US2011/058820 Search Report and Written Opinion dated Jun. 21, 2012.
Rafi, et al., Modulation of bcl-2 and Cytotoxicity by Licochalcone-A, a Novel Estrogenic Flavonoid. Anticancer Res. 2000; 20:2653-58.
Ravindranath, et al., Anticancer Therapeutic Potential of Soy Isoflavone, Genistein. Complementary and Alternative Approaches to Biomedicine, edited by Edwin L. Cooper and Nobuo Yamaguchi. Kluwer Academic/Plenum Publishers. 2004; 121.
Registration No. 1157-39-7, 4H-1-Benzopyran-4-one, 7-methoxy-3-(4-methoxyphenyl)-methyl-(9CI), Nov. 16, 1984.
Registration No. 116703-40-3, 4H-1-Benzopyran-4-one, 2,3-dihydro-7,8-dimethoxy-3-(4-methoxyphenyl)- (9CI), Oct. 2, 1988.
Registration No. 116703-49-2, 4H-1-Benzopyran-4-one, 2,3-dihydro-7,8-dihydroxy-3-(4-methoxyphenyl)- (9CI), Oct. 2, 1988.
Registration No. 116718-51-5, 4H-1-Benzopyran-4-one, 7-hydroxy-3-(4-methoxyphenyl)-8-methyl-methyl-(9CI), Oct. 2, 1988.

(56) References Cited

OTHER PUBLICATIONS

Registration No. 124093-18-1, 4H-1-Benzopyran-4-one, 2,3-dihydro-7-hydroxy-3-(4-hydroxy-3- methoxyphenyl)-(9CI), Dec. 1, 1989.
Registration No. 129159-04-2, 4H-1-Benzopyran-4-one, 2,3-dihydro-3-(4-hydroxyphenyl)-(9CI), Aug. 31, 1990.
Registration No. 129159-05-3, 4H-1-Benzopyran-4-one, 3-(3,4-dihydroxyphenyl)-2,3-dihydro-(9CI), Aug. 31, 1990.
Registration No. 13139-86-1, Magnesium, bromo(4-methoxyphenyl)-(9CI), Nov. 16, 1984.
Registration No. 142050-44-0, 4H-1-Benzopyran-4-one, 7-hydroxy-3-[4-methoxy-3-(methoxy-t3)phenyl]- (9CI), Jun. 26, 1992.
Registration No. 143358-24-1, 4H-1-Benzopyran-4-one, 2,3-dihydro-7-methoxy-3-(4-methoxyphenyl)-(+)- (9CI), Sep. 9, 1992.
Registration No. 143358-39-8, 4H-1-Benzopyran-4-one, 2,3-dihydro-7-methoxy-3-(4-methoxyphenyl)-(−) (9CI), Sep. 9, 1992.
Registration No. 15236-11-0, 4H-1-Benzopyran-4-one, 2,3-dihydro-7-methoxy-3-(4-methoxyphenyl)-(9CI), Nov. 16, 1984.
Registration No. 16750-63-3, Magnesium, bromo(2-methoxyphenyl)-(9CI), Nov. 16, 1984.
Registration No. 201678-33-3, 4H-1-Benzopyran-4-one, 3-(3,4-dimethoxyphenyl) -2,3-dihydro-7,8- dimethoxy-(9CI), Feb. 22, 1998.
Registration No. 206257-38-7, 4H-1-Benzopyran-4-one, 2, 3-dihydro-3-(4-hydroxyphenyl)-7-methoxy-(9CI), Jun. 3, 1998.
Registration No. 24160-14-3 , 4H-1-Benzopyran-4-one, 3-(3,4-dimethoxyphenyl)-7-hydroxy-(9CI), Nov. 16, 1984.
Registration No. 288267-24-3, 4H-1-Benzopyran-4-one, 7-hydroxy-3-(4-hydroxy-3-methoxyphenyl)-8- methyl-(9CI), Sep. 6, 2000.
Registration No. 304892-19-1, 4H-1-Benzopyran-4-one, 3-(3,4-dihydroxyphenyl)-2,3-dihydro-7-hydroxy-(9CI), Nov. 29, 2000.
Registration No. 36282-40-3, Magnesium, bromo(3-methoxyphenyl)-, Nov. 16, 1984.
Registration No. 39604-72-3, 4H-1-Benzopyran-4-one, 2,3-dihydro-7methoxy-3-(4-methoxyphenyl)-8- methyl-(9CI), Nov. 16, 1984.
Registration No. 4626-22-6, 4H-1-Benzopyran-4-one, 2,3-dihydro-7-hydroxy-3-(4-methoxyphenyl)-(9CI), Nov. 16, 1984.
Registration No. 67492-31-3, 4H-1-Benzopyran-4-one, 2,3-dihydro-7-hydroxy-3-(3-hydroxy-4- methoxyphenyl)-(9CI), Nov. 16, 1984.
Registration No. 680195-83-9, 4H-1-Benzopyran-4-one, 2,3-dihydro-7,8-dihydroxy-3-(4-hydroxyphenyl)- (9CI), May 6, 2004.
Registration No. 83206-83-1, 4H-1-Benzopyran-4-one, 3-(3,4-dimethoxyphenyl)-2,3-dihydro-7-hydroxy-(9CI), Nov. 16, 1984.
Registration No. 85915-64-6, 2H-1-Benzopyran-7-ol, 4-[5-(3,4-dihydro-7-hydroxy-2-H-1-benzopyran-3-yl)-4-hydroxy-2-methoxyphenyl]-3,4-dihydro-3-(2-hydroxy-4-methoxyphenyl)-, [3S-[3α-4β(R*)]]-(9CI), date unavailable.
Registration No. 85915-66-8, 2H-1-Benzopyran,4-[5-(3,4-dihydro-7-methoxy-2H-1-benzopyran-3-yl)-2,4- dimethoxyphenyl]-3-(2,4-dimethoxyphenyl)-3,4-dihydro-7-methoxy-,[3S-[3α4β(R*)]]-(9CI), date unavailable.
Registration No. 95307-73-6, 4H1-Benzopyran-4-one-2-d, 2,3-dihydro-2-d-7-hydroxy-3-(4- methoxyphenyl)-(9CI), Mar. 16, 1985.
Registration No. 95457-39-9, 4H-1-Benzopyran-4-one-4-14C, 3-(3,4-dimethoxyphenyl)-7-hydroxy-(9CI), Mar. 23, 1985.
Registration No. 95541-42-7, 1,3-Benzenediol, 4-[3,4-dihydro-3-(2-hydroxy-4-methoxyphenyl)-7-methoxy-2H-1-benzopyran-4-yl]-,(3R-trans)-(9CI), date unavailable.
Registration No. 95541-43-8, 2H-Benzopyran,3,4-bis(2,4-dimethoxyphenyl)-3,4-dihydro-7-methoxy-,(3R-trans)-(9CI), date unavailable.
Registration No. 95541-44-9, 1,3,5-Benzenetriol,2-[3,4-dihydro-3-(2-hydroxy-4-methoxyphenyl)-7- methoxy-2H-1-benzopyran-4-yl]-,(3R-trans)-(9CI), date unavailable.
Registration No. 95541-45-0, 1,3,5-Benzenetriol,2,4-bis[3,4-dihydro-3-(2-hydroxy-4-methoxyphenyl)-7- methoxy-2H-1-benzopyran-4-yl]-,[3R-[3α,4β(3R*,4S"])-(9CI), date unavailable.
Registration No. 95541-46-1, 2H-1-Benzopyran,3-(2,4-dimethoxyphyenyl)-3,4-dihydro-7-methoxy-4(2,4,6-trimethoxyphenyl)-,(3R-trans)-(9CI), date unavailable.
Registration No. 95541-51-8, 2H-1-Benzopyran-7-ol,3-[3,4-dihydro-3-(2-hydroxy-4-methoxyphenyl)-7- methoxy-2H-1-benzopyran-4-yl]-2-hydroxy-4-methoxyphenyl]-3,4-dihydro-, [3R-3α,4β(S*)]]-(9CI), date unavailable.
Registration No. 95541-53-0, 2H-1-Benzopyran,4-[5(3,4-dihyrdro-7-methoxy-2H-1-benzopyran-3-y1)-2,4- dimethoxyphenyl]-3-(2,4-dimethoxyphenyl)-3,4-dihydro-7-methoxy-,[3R-[3α,4β(S*)]]-(9CI), date unavailable.
Registration No. 95541-54-1, 2H-1-Benzopyran-7-ol,3-[-[4-dihydro-4-[4-hydroxy-5-(7-hydroxy-2H-1- benzopyran-3-y1)-2-methoxyphenyl]-3-(2-hydroxy-4-methon/phenyl)-(3S-trans)-(9CI), date unavailable.
Registration No. 95541-57-4, 2H-1-Benzopyran,4-[2,4-dimethoxy-5-(7-methoxy-2H-1-benzopyran-3-yl)phenyl]-3-(2,4-dimethoxyphenyl)-3,4-dihydro-7-methoxy-,(3S-trans)-(9CI), date unavailable.
Registration No. 95541-66-5, 2H-1-Benzopyran,4-(2,4-dimethoxyphenyl)-3,4-dihydro-7-methoxy-3-[4- methoxy-2-(methoxymethoxy)phenyl]-,(3R-trans)-(9CI), date unavailable.
Registration No. 95762-78-0, 2H-1-Benzopyran,4,4'-(2,4,6-trimethoxy-1,3-phenylene)bix[3-(2,4- dimethoxyphenyl)-3,4-dihyrdo-7-methoxy-,[3R[3α,4β(3'R*,4'S*)]]-(9CI), date unavailable.
Scambia, et al., Antiproliferative effect of silybin on gynaecological malignancies;synergism with cisplatin and doxorubicin. Eur J Cancer. May 1996; 32A(5):877-82 (Abstract Only in English).
Scambia, Synergistic antiproliferative activity of quercetin and cisplatin on ovarian cancer cell growth. Anti-Cancer Drugs Oct. 1990; 1(1):45-8 (Abstract Only in English).
Sepulveda-Boza, et al., The preparation of new isoflavones, Synthetic Communications. 2001; 3(12):1933-40.
Szlosarek, et al., Tumour necrosis factor a: a potential target for the therapy of solid tumours. The Lancet Oncology. Sep. 2003; 4:565-73.
Tamura, et al., Genistein Enhances the Cisplatin-Induced Inhibition of Cell Growth and Apoptosis in Human Malignant Melanoma Cells. Pigment Cell Res. 2003; 16:470-76 (Abstract Only in English).
Teo, et al., Synthesis of 3-(p-fluorophenyl)-4-arylchrom-3-enes as selective ligands for antiestrogen-binding sites. J Chem Res. Synopses. 1990; 1:4-5 (Abstract Only in English).
Teo, et al., Synthesis of arylchromenes and arylchromans. Bulletin of the Singapore National Institute of Chemistry. 1994; 22:69-74 (Abstract Only in English).
Therasse et al., New guidelines to evaluate the response to treatment in solid tumors. J. Natl. Cancer Inst., 92 (3): 205-216 (2000).
Todorov, et al., Role of a proteolysis-inducing factor(PIF) in a cachexia induced by a human melanoma(G361). Br J Cancer. 1999; 80(11):1734-37.
Varady, The flavonoids of Podocarpus spicatus. I. Structure of podospicatin. Synthesis of podospicatin mono-,di-, and trimethyl ethers. Periodica Polytech. 1963; 7(4):241-58 (Abstract Only in English).
Verma et al., Smooth Conversion of 3,4-Diarylcoumarins and 3,4,5-Triaryl-2(5H)-furanones to 2H-Chromene and 2,5-Dihydrofuran Derivatives with Dimethyl Sulfide-Borane Complex. Synthesis. 1988; 1:68-70.
Voss, et al., New isoflavonoids as inhibitors of porcine 5-lipoxygenase Biochem Pharmacol. 1992; 44(1):157-62 (Abstract Only in English).
Waud, et al., Antitumor drug cross-resistance in vivo in a cisplatin-resistant murine P388 leukemia, Cancer Chemotherapy and Pharmacology. 1991; 27(6):456-63 (Abstract Only in English).
Weidenborner, et al., Control of storage fungi of the genus *Aspergillus* on legumes with flavonoids and isoflavonoids. Angewandte Botanik. 1990; 64(1-2):175-90 (Abstract Only in English).

(56) References Cited

OTHER PUBLICATIONS

Wolfbeis, et al., The Absorption and Fluorescence of Isoflavones and the Effect of Shift Reagents. Z Naturforsch. Sep. 23, 1984; 39b:238-43.
Zyner, et al., Platinum(II) and palladium(II) N,O-Chelates with substituted flavanone containing ligangs. Acta Pol Pharm. 1999; 56(2):159-67.
Zyner, et al., Pt(II) and Pt(II) complexes of 3-aminoflavone: In vitro and in vivo evaluation. Pharmazie. 1999; 54(12):945-46.
U.S. Appl. No. 13/881,609 Notice of Allowance mailed Jan. 13, 2017.
U.S. Appl. No. 13/881,609 Office Action mailed Apr. 10, 2015.
U.S. Appl. No. 13/881,609 Office Action dated May 16, 2016.
U.S. Appl. No. 13/881,609 Office Action mailed Aug. 7, 2015.

* cited by examiner

ISOFLAVONOID COMPOSITIONS AND METHODS FOR THE TREATMENT OF CANCER

CROSS-REFERENCE

This application is filed pursuant to 35 U.S.C. §371 as a United States National Phase Application of International Application Ser. No. PCT/US2011/058820, filed Nov. 1, 2011, which claims the benefit of priority to U.S. Provisional Application No. 61/408,972, filed Nov. 1, 2010, each of which application is incorporated herein by reference in their entirety.

BACKGROUND OF THE INVENTION

Cancer is the leading cause of death worldwide.

SUMMARY OF THE INVENTION

Provided herein are pharmaceutical compositions, methods of treating disease, and kits. Provided in certain embodiments herein is a composition, wherein the composition comprises an isoflavonoid derivative and a cyclodextrin. In some embodiments, the composition comprises a liquid vehicle(s) to provide a physiologically acceptable formulation for parenteral administration. Certain embodiments of the present invention provide a method for the treatment of cancer comprising administration of the composition to an individual in need of cancer therapy.

Some embodiments of the present invention describe a pharmaceutical composition comprising a compound (i.e., isoflavonoid derivative) of general formula I:

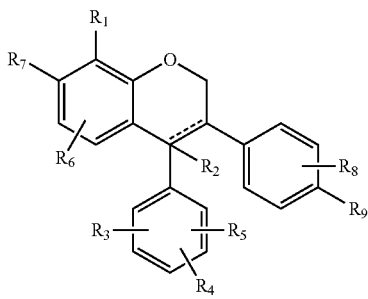

(I)

wherein:
$R_1$ is hydrogen, hydroxy, halo, $NR_{10}R_{11}$, $C_{3-6}$ cycloalkyl, $C_{1-6}$ alkoxy, $C_{2-6}$ alkenyl, $C_{1-6}$ fluoroalkyl or $C_{1-6}$ alkyl optionally substituted by one or more hydroxy, chloro, bromo, iodo or $NR_{10}R_{11}$ groups;
the drawing ==== and $R_2$ together represent a double bond or the drawing ==== represents a single bond and $R_2$ is hydrogen, hydroxy, $NR_{10}R_{11}$, $C_{1-3}$ alkoxy, $C_{1-3}$ fluoroalkyl, halo or $C_{1-3}$ alkyl optionally substituted by one or more hydroxy, chloro, bromo, iodo or $NR_{10}R_{11}$ groups;
$R_3$ is hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, $(O)_nC_{1-4}$alkylene$NR_{14}R_{15}$ or $C_{1-6}$ alkyl optionally substituted by one or more hydroxy, chloro, bromo, iodo or $NR_{10}R_{11}$ groups;
$R_4$, $R_5$, $R_6$, $R_7$, $R_8$, and $R_9$ are independently hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, or $C_{1-6}$ alkyl optionally substituted by one or more hydroxy, chloro, bromo, iodo or $NR_{10}R_{11}$ groups;
$R_{10}$, $R_{11}$, and $R_{12}$ are independently hydrogen, $C_{1-6}$ alkyl, $C_{3-6}$ cycloalkyl, or trialkyl silyl;
$R_{13}$ is hydrogen, $C_{1-6}$ alkyl, $C_{3-6}$ cycloalkyl or $NR_{10}R_{11}$;
n represents 0 or 1; and
$R_{14}$ and $R_{15}$ independently represent hydrogen or $C_{1-6}$ alkyl or $NR_{14}R_{15}$ when taken together represents a 5 or 6 membered heteroaromatic or heterocyclic,
or a pharmaceutically acceptable salt thereof; and
a cyclodextrin.

In some embodiments, the pharmaceutical composition comprises a compound (i.e., isoflavonoid derivative) of formula II:

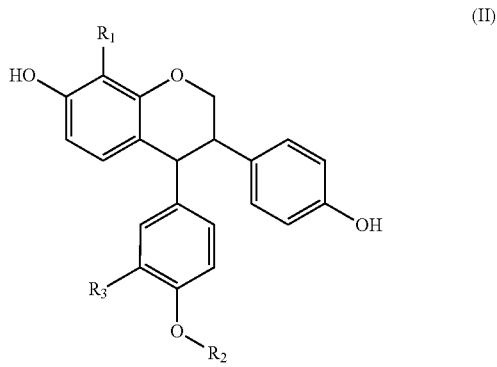

(II)

wherein:
$R_1$, $R_2$, and $R_3$ are independently hydrogen or methyl
or a pharmaceutically acceptable salt thereof; and
a cyclodextrin.

In specific embodiments, $R_1$ is hydrogen. In other embodiments, $R_1$ is methyl. In further or additional embodiments, $R_2$ is hydrogen. In some embodiments, $R_2$ is methyl. In further or additional embodiments, $R_3$ is hydrogen. In some embodiments, $R_3$ is methyl.

In some embodiments, the cyclodextrin of a composition described herein comprising either a compound of formula I or II is a solubilizing cyclodextrin. In certain embodiments, the cyclodextrin or solubilizing cyclodextrin is selected from the group consisting of SAE-CD derivatives, SBE-α-CD, SBE-β-CD, SBE1-β-CD, SBE4-β-CD, SBE7-β-CD, SBE-γ-CD, hydroxypropyl-β-cyclodextrin, 2-HP-β-CD, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, and derivatives and/or combinations thereof. In certain embodiments, the composition comprises SBE7-β-CD. In some embodiments, the composition comprises about 0.5 to 50%, about 2 to 48%, about 5 to 45%, about 10 to 43%, about 15 to 40%, about 22 to 37%, about 25 to 35%, about 28 to 32% w/v SBE7-β-CD. In specific embodiments, the composition comprises about 30% w/v SBE7-β-CD.

In some embodiments, the composition further comprises a liquid vehicle. In some embodiments, the liquid vehicle is aqueous. In specific embodiments, the liquid vehicle is isotonic or hypotonic. In other embodiments, the liquid vehicle comprises a water miscible, physiologically acceptable solvent. In some embodiments, the composition further comprises one or more of lactose, dextrose, mannitol, pH buffering agents, antioxidant agents, preservative agents, tonicity adjusters or a combination thereof.

In some embodiments, the composition comprises a compound of formula I or II in an amount of about 0.2-50 mg/mL. In specific embodiments, the composition comprises a compound of formula I or II in an amount of about 25-40 mg/mL.

In some embodiments, the composition further comprises a chemotherapeutic agent selected from the group consisting of cisplatin, carboplatin, paclitaxel, gemcitabine or doxorubicin.

Also described herein is a composition comprising a compound of formula II and a cyclodextrin for use in inducing apoptosis in a cancer cell. In some embodiments, the type of cancer cell apoptosed, or otherwise targeted, is selected from the group consisting of bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer and cancers of the brain. In certain embodiments, the type of cancer cell is human breast, prostate, ovarian, pancreatic, or cervical cancer. In certain specific embodiments, the type of cancer cell is human breast cancer or ovarian cancer.

In certain embodiments, provided herein is a method of inducing apoptosis in a cancer cell. In some embodiments, the method comprises contacting the cancer cell with the composition comprising any compound described herein (i.e., isoflavonoid derivative), such as a compound of formula II and a cyclodextrin.

In some embodiments, the cyclodextrin of a composition or used in a method described herein comprises either a compound of formula I or II is a solubilizing cyclodextrin. In certain embodiments, the cyclodextrin or solubilizing cyclodextrin is selected from the group consisting of SAE-CD derivatives, SBE-α-CD, SBE-β-CD, SBE1-β-CD, SBE4-β-CD, SBE7-β-CD, SBE-γ-CD, hydroxypropyl-β-cyclodextrin, 2-HP-β-CD, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, and derivatives and/or combinations thereof. In certain embodiments, the composition comprises SBE7-β-CD. In some embodiments, the composition comprises about 0.5 to 50%, about 2 to 48%, about 5 to 45%, about 10 to 43%, about 15 to 40%, about 22 to 37%, about 25 to 35%, about 28 to 32% w/v SBE7-β-CD. In certain specific embodiments, the composition comprises about 30% w/v SBE7-β-CD.

In some embodiments, any composition described herein further comprises, or a method described herein comprises administering an isoflavonoid derivative and a cyclodextrin together with, a liquid vehicle. In some embodiments, the liquid vehicle is aqueous. In specific embodiments, the liquid vehicle is isotonic or hypotonic. In other embodiments, the liquid vehicle comprises a water miscible, physiologically acceptable solvent. In some embodiments, the composition further comprises one or more of lactose, dextrose, mannitol, pH buffering agents, antioxidant agents, preservative agents, tonicity adjusters or a combination thereof.

In some embodiments, the composition comprises a compound of formula II in an amount of about 0.2-50 mg/mL. In specific embodiments, the composition comprises a compound of formula II in an amount of about 25-40 mg/mL.

In some embodiments, the type of cancer cell apoptosed, or otherwise targeted according to any method described herein, is selected from the group consisting of bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer and cancers of the brain. In certain embodiments, the type of cancer cell is human breast, prostate, ovarian, pancreatic, or cervical cancer. In certain specific embodiments, the type of cancer cell is human breast cancer or ovarian cancer.

In some embodiments, any method described herein further comprises administering, e.g., to a targeted cell, a chemotherapeutic agent. In specific embodiments, the chemotherapeutic agent is selected from the group consisting of cisplatin, carboplatin, paclitaxel, gemcitabine or doxorubicin.

In certain embodiments, a cancer cell apoptosed, or otherwise targeted according to any method described herein, is present in an individual. In specific embodiments, the individual is in need of cancer therapy. In certain specific embodiments, the composition is administered to the individual intravenously.

Also described herein is a composition comprising a compound of formula II and a cyclodextrin for use in the treatment of cancer in an individual in need of cancer therapy.

In some embodiments, provided herein is a method of treating cancer in an individual in need of cancer therapy. In certain embodiments, the method comprises administering to the individual the composition comprising a compound (i.e., isoflavonoid derivative) of formula II and a cyclodextrin.

In some embodiments, provided herein is a method of treating cancer in an individual, the method comprising administering cyclodextrin in combination with a compound of formula I or II. In specific embodiments, the cyclodextrin is a solubilizing cyclodextrin. In certain embodiments, the cyclodextrin or solubilizing cyclodextrin is selected from the group consisting of SAE-CD derivatives, SBE-α-CD, SBE-β-CD, SBE1-β-CD, SBE4-β-CD, SBE7-β-CD, SBE-γ-CD, hydroxypropyl-β-cyclodextrin, 2-HP-β-CD, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, and derivatives and/or combinations thereof. In certain embodiments, the composition comprises SBE7-β-CD. In some embodiments, the composition comprises about 0.5 to 50%, about 2 to 48%, about 5 to 45%, about 10 to 43%, about 15 to 40%, about 22 to 37%, about 25 to 35%, about 28 to 32% w/v SBE7-β-CD. In certain specific embodiments, the composition comprises about 30% w/v SBE7-β-CD.

In some embodiments, a cyclodextrin and a compound of formula II is administered in combination with a liquid vehicle. In some embodiments, the liquid vehicle is aqueous. In specific embodiments, the liquid vehicle is isotonic or hypotonic. In other embodiments, the liquid vehicle comprises a water miscible, physiologically acceptable solvent. In some embodiments, the composition further comprises one or more of lactose, dextrose, mannitol, pH buffering agents, antioxidant agents, preservative agents, tonicity adjusters or a combination thereof.

In some embodiments, a method described herein comprises administering to an individual a compound of formula II in an amount of about 0.2-50 mg/mL of composition administered. In specific embodiments, the composition comprises a compound of formula II in an amount of about 25-40 mg/mL. In more specific embodiments, the composition comprises a compound of formula II in an amount of about 30 mg/mL, or about 35 mg/mL.

In some embodiments, provided herein is a method of treating cancer by administering any composition or combination described herein (e.g., cyclodextrin in combination with a compound of formula I or II), wherein the cancer is bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer or a cancer of the brain. In certain embodiments, the type of cancer is human breast, prostate, ovarian, pancreatic, or cervical cancer. In certain specific embodiments, the type of cancer is human breast cancer or ovarian cancer. In more specific embodiments, the cancer is human breast cancer. In other specific embodiments, the cancer is human ovarian cancer.

In some embodiments, any method of treating cancer described herein further comprises administering to the individual a chemotherapeutic agent. In specific embodiments, the chemotherapeutic agent is selected from the group consisting of cisplatin, carboplatin, paclitaxel, gemcitabine or doxorubicin. In certain specific embodiments, the composition is administered to the individual intravenously.

Some embodiments provided herein describe a composition comprising a compound of formula II and a cyclodextrin for use in increasing, inducing, or restoring sensitivity of a cancer cell to a chemotherapeutic agent, anti-cancer agent or radiation therapy. In some embodiments, the cancer cell has lost sensitivity to a chemotherapeutic agent, anti-cancer agent or radiation therapy.

In other embodiments, provided herein is a method of increasing, inducing, or restoring sensitivity of a cancer cell to a chemotherapeutic agent or radiation therapy. In certain embodiments, the method comprises contacting said cell with a composition comprising a compound (i.e., isoflavonoid derivative) of formula II and a cyclodextrin.

In some embodiments, the type of cancer cell sensitized according to a method described herein is bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer or a cancer of the brain. In certain embodiments, the type of cancer cell is human breast, prostate, ovarian, pancreatic, or cervical cancer. In certain specific embodiments, the type of cancer cell is human breast cancer or ovarian cancer. In more specific embodiments, the cancer cell is a human breast cancer cell. In other specific embodiments, the cancer cell is a human ovarian cancer cell.

In certain embodiments, the cancer cell sensitized according to a method described herein is present in an individual. In specific embodiments, the individual is in need of cancer therapy. In certain specific embodiments, the composition is administered to the individual intravenously. In some embodiments, the cancer cell has lost sensitivity to a chemotherapeutic agent or radiation therapy.

In some embodiments, a kit provided herein has a sealable, plastic infusion bag and a pharmaceutical composition, wherein the composition comprises any isoflavonoid derivative described herein (e.g., a compound of formula I or a compound of formula II) and a cyclodextrin (e.g., a solubilizing cyclodextrin). In some embodiments, the kit further comprises intravenous tubing. In still further embodiments, the kit further comprises a needle.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

There is a continuing need to develop and provide effective therapies for the treatment of cancer. Described herein is a composition that has anti-cancer activity. The composition described herein comprises isoflavonoid derivatives (substituted diaryl chroman derivatives) and a cyclodextrin (e.g., a cyclodextrin that enhances the solubility of the isoflavonoid derivative). Also provided herein are methods to induce apoptosis in a cancer cell, methods to treat cancer in individuals in need of cancer therapy, and methods to increase sensitivity of a cancer cell to a chemotherapeutic agent and/or radiation therapy (or to sensitize an individual to a particular chemotherapy).

Certain Definitions

Unless otherwise noted, terminology used herein should be given its normal meaning as understood by one of skill in the art.

The term "alkyl" as used herein refers to saturated or unsaturated, straight- or branched-chain hydrocarbon radicals derived from a hydrocarbon moiety containing between one and twenty carbon atoms by removal of a single hydrogen atom. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkenyl" as used herein refers to unsaturated, straight- or branched-chain hydrocarbon radicals derived from a hydrocarbon moiety containing between two and twenty carbon atoms by removal of a single hydrogen atom.

The terms "$C_1$-$C_3$-alkyl" and "$C_1$-$C_6$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$-$C_3$-alkyl radicals include methyl, ethyl, propyl and isopropyl. Examples of $C_1$-$C_6$-alkyl radicals include, but not limited to, methyl, ethyl, propyl, isopropyl, n-butyl, tert-butyl, neopentyl and n-hexyl.

The term "cycloalkyl" as used herein refers to a monovalent group derived from a monocyclic or bicyclic saturated carbocyclic ring compound containing between three and twenty carbon atoms by removal of a single hydrogen atom.

The term "$C_3$-$C_6$ cycloalkyl" denoted a monovalent group derived from a monocyclic or bicyclic saturated carbocyclic ring compound by removal of a single hydrogen atom. Examples include cyclopropyl, cyclobutyl, cyclopentyl, cyclohexyl.

The alkyl group or cycloalkyl group may optionally be substituted by one or more of fluorine, chlorine, bromine, iodine, carboxyl, $C_{1-4}$ alkoxycarbonyl, $C_{1-4}$ alkylaminocarbonyl, di-($C_{1-4}$ alkyl)-aminocarbonyl, hydroxyl, $C_{1-4}$ alkoxy, formyloxy, $C_{1-4}$ alkylcarbonyloxy, $C_{1-4}$ alkylthio, $C_{3-6}$ cycloalkyl or phenyl.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The terms "$C_1$-$C_3$-alkoxy", "$C_1$-$C_6$-alkoxy" as used herein refers to the $C_1$-$C_3$-alkyl group and $C_1$-$C_6$-alkyl group, as previously defined, attached to the parent molecular moiety through an oxygen atom. Examples of $C_1$-$C_6$-alkoxy radicals include, but not limited to, methoxy, ethoxy, propoxy, isopropoxy, n-butoxy, tert-butoxy, neopentoxy and n-hexoxy.

The term "halo" and "halogen" as used herein refer to an atom selected from fluorine, chlorine, bromine and iodine.

The term "fluoroalkyl" includes "alkyl" wherein one or more such as 1, 2, 3, 4, or 5 of the hydrogens have been replaced by fluoro. The fluoroalkyl may be straight chain or branched chain "alkyl" unit. Preferred fluoroalkyl groups include trifluoromethyl and pentafluoroethyl.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. For example, S. M. Berge, et al. describes pharmaceutically acceptable salts in detail in J. Pharmaceutical Sciences, 66: 1-19 (1977), incorporated herein by reference for this purpose. The salts are prepared in situ during the final isolation and purification of the compounds described herein, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "cyclodextrin," as used herein, refers to cyclic carbohydrates consisting of at least six to eight glucose molecules in a ring formation. The outer part of the ring contains water soluble groups; at the center of the ring is a relatively nonpolar cavity able to accommodate small molecules.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. An appropriate "effective" amount in any individual case may be determined using techniques, such as a dose escalation study.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease).

The term "carrier" as used herein, refers to relatively nontoxic chemical compounds or agents that facilitate the incorporation of a compound into cells or tissues.

Compounds

Some embodiments of the present invention describe a pharmaceutical composition comprising a compound (i.e., isoflavonoid derivative) of general formula I:

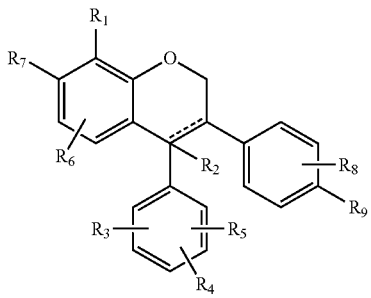

(I)

wherein:
$R_1$ is hydrogen, hydroxy, halo, $NR_{10}R_{11}$, $C_{3-6}$ cycloalkyl, $C_{1-6}$ alkoxy, $C_{2-6}$ alkenyl, $C_{1-6}$ fluoroalkyl or $C_{1-6}$ alkyl optionally substituted by one or more hydroxy, chloro, bromo, iodo or $NR_{10}R_{11}$ groups;
the drawing ==== and $R_2$ together represent a double bond or the drawing ==== represents a single bond and $R_2$ is hydrogen, hydroxy, $NR_{10}R_{11}$, $C_{1-3}$ alkoxy, $C_{1-3}$ fluoroalkyl, halo or $C_{1-3}$ alkyl optionally substituted by one or more hydroxy, chloro, bromo, iodo or $NR_{10}R_{11}$ groups;
$R_3$ is hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, $(O)_nC_{1-4}$alkyleneNR_{14}R_{15}$ or $C_{1-6}$ alkyl optionally substituted by one or more hydroxy, chloro, bromo, iodo or $NR_{10}R_{11}$ groups;
$R_4$, $R_5$, $R_6$, $R_7$, $R_8$, and $R_9$ are independently hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, or $C_{1-6}$ alkyl optionally substituted by one or more hydroxy, chloro, bromo, iodo or $NR_{10}R_{11}$ groups;
$R_{10}$, $R_{11}$, and $R_{12}$ are independently hydrogen, $C_{1-6}$ alkyl, $C_{3-6}$ cycloalkyl, or trialkyl silyl;
$R_{13}$ is hydrogen, $C_{1-6}$ alkyl, $C_{3-6}$ cycloalkyl or $NR_{10}R_{11}$;
n represents 0 or 1; and
$R_{14}$ and $R_{15}$ independently represent hydrogen or $C_{1-6}$ alkyl or $NR_{14}R_{15}$ when taken together represents a 5 or 6 membered heteroaromatic or heterocyclic,
or a pharmaceutically acceptable salt thereof; and
a cyclodextrin.

In some embodiments, the pharmaceutical composition comprises a compound (i.e., isoflavonoid derivative) of formula II:

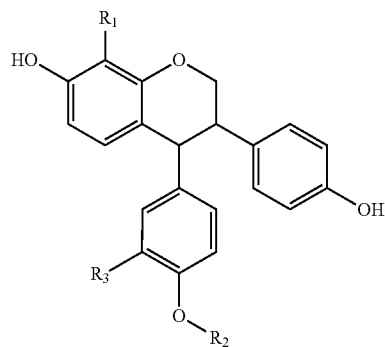

(II)

wherein:
$R_1$, $R_2$, and $R_3$ are independently hydrogen or methyl
or a pharmaceutically acceptable salt thereof; and
a cyclodextrin.

In some embodiments, $R_1$ is $C_1$-$C_6$alkyl. In other embodiments, $R_1$ is $C_1$-$C_3$alkyl. In other embodiments, $R_1$ is $C_1$-$C_2$alkyl. In specific embodiments, $R_1$ is hydrogen. In other embodiments, $R_1$ is methyl. In other embodiments, $R_1$ is ethyl. In other embodiments, $R_1$ is propyl. In other embodiments, $R_1$ is iso-propyl. In other embodiments, $R_1$ is butyl. In other embodiments, $R_1$ is iso-butyl. In other embodiments, $R_1$ is sec-butyl. In other embodiments, $R_1$ is tert-butyl. In other embodiments, $R_1$ is pentyl. In other embodiments, $R_1$ is hexyl.

In some embodiments, $R_2$ is $C_1$-$C_6$alkyl. In other embodiments, $R_2$ is $C_1$-$C_3$alkyl. In other embodiments, $R_2$ is $C_1$-$C_2$alkyl. In further or additional embodiments, $R_2$ is hydrogen. In some embodiments, $R_2$ is methyl.

In further or additional embodiments, $R_3$ is $C_1$-$C_6$alkyl. In other embodiments, $R_3$ is $C_1$-$C_3$alkyl. In other embodiments, $R_3$ is $C_1$-$C_2$alkyl. In some embodiments, $R_3$ is methyl. In some embodiments, $R_3$ is ethyl. In some embodiments, $R_3$ is propyl. In some embodiments, $R_3$ is iso-propyl. In some embodiments, $R_3$ is butyl. In some embodiments, $R_3$ is iso-butyl. In some embodiments, $R_3$ is sec-butyl. In some embodiments, $R_3$ is tert-butyl. In some embodiments, $R_3$ is pentyl. In some embodiments, $R_3$ is or hexyl. In other embodiments, $R_3$ is hydrogen.

Specific compounds of formula I and II are shown below:

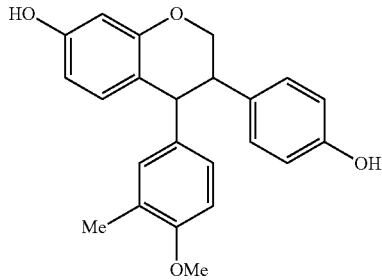
(1)

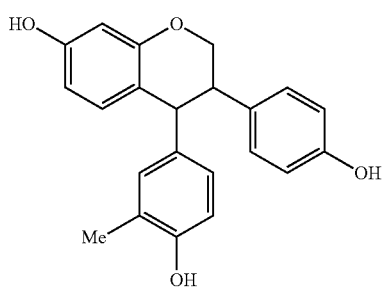
(2)

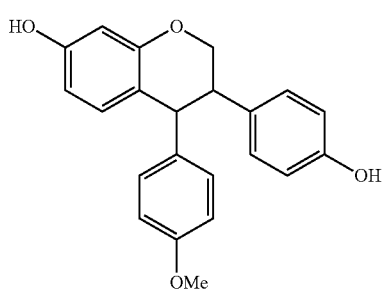
(3)

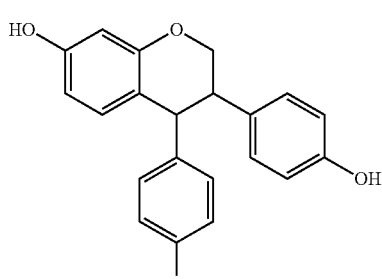
(4)

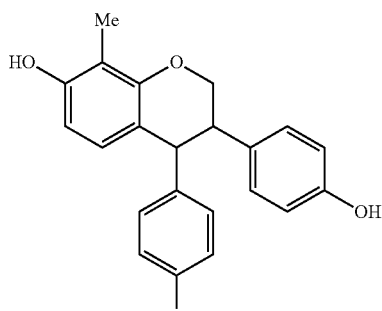
(5)

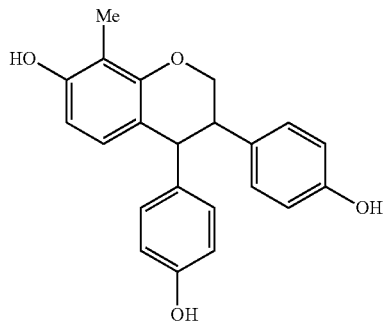
(6)

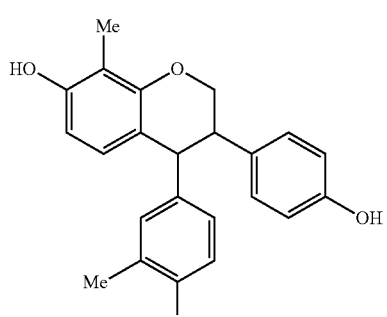
(7)

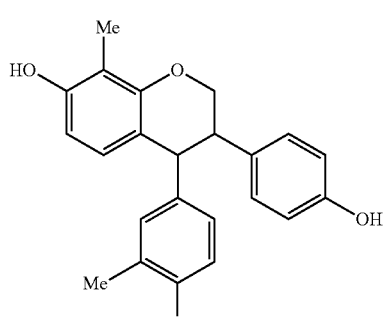
(8)

or salts or a derivative thereof.

In specific embodiments, a compound of Formula I or II include:

3-(4-hydroxyphenyl)-4-(4-methoxy-3-methylphenyl)chroman-7-ol (1);

3-(4-hydroxyphenyl)-4-(4-hydroxy-3-methylphenyl)chroman-7-ol (2);

3-(4-hydroxyphenyl)-4-(4-methoxyphenyl)chroman-7-ol (3);

3-(4-hydroxyphenyl)-4-(4-hydroxyphenyl)chroman-7-ol (4);

3-(4-hydroxyphenyl)-4-(4-methoxyphenyl)-8-methylchroman-7-ol (5);

3-(4-hydroxyphenyl)-4-(4-hydroxyphenyl)-8-methylchroman-7-ol (6);

3-(4-hydroxyphenyl)-4-(4-methoxy-3-methylphenyl)-8-methylchroman-7-ol (7); and 3-(4-hydroxyphenyl)-4-(4-hydroxy-3-methylphenyl)-8-methylchroman-7-ol (8).

In the compounds according to certain embodiments of the invention, the aryl substituents on the heterocyclic ring are cis or trans relative to each other. Preferably in the compounds of formula I and II according to certain embodiments of the invention, these substituents will be cis.

The compounds of formula I and II according to some embodiments of this invention include two chiral centers.

The present invention includes all the enantiomers and diastereomers as well as mixtures thereof in any proportions. The invention also extends to isolated enantiomers or pairs of enantiomers. Diastereomeric mixtures can be separated into their individual diastereomers on the basis of their physical chemical differences by methods such as chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The compounds of formula I and II according to some embodiments are racemic mixture. In other embodiments, any compound described herein is in the optically pure form (e.g., optically active (+) and (−), (R)- and (S)-, d or l, or (D)- and (L)-isomers). In certain preferred embodiments, a compound of formula I and II is the d-isomer. Accordingly, provided herein, in some embodiments, is the optically active d-isomer having a structure of formula I and II in enantiomeric excess. In some embodiments, the d-isomer of a compound of formula I and II is provided in at least 50%, 55%, 60%, 65%, 70%, 75%, 80%, 85%, 88%, 90%, 91%, 92%, 93%, 94%, 95%, 96%, 97%, 98%, 99%, 95.5%, or 99.9% enantiomeric excess. In other embodiments, the d-isomer of a compound of formula I and II is provided in greater than 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess. In specific embodiments, a compound of formula I and II has greater than 95% enantiomeric excess.

Specific optically active compounds of formula I and II are shown below:

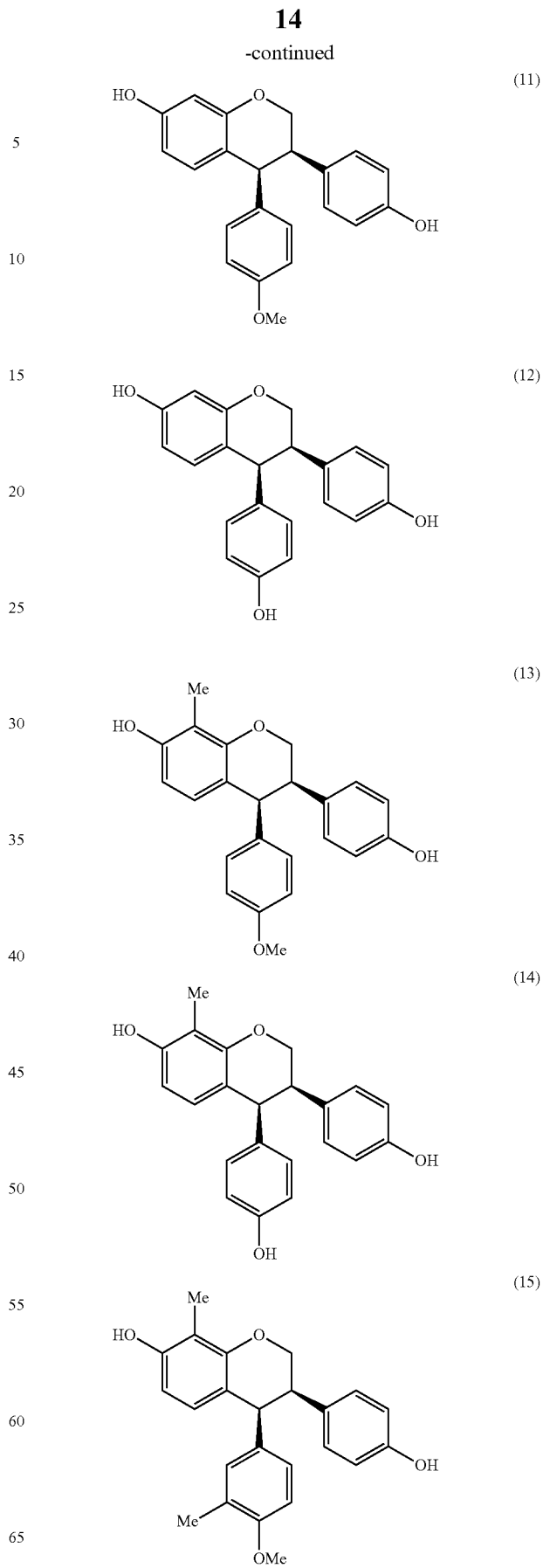

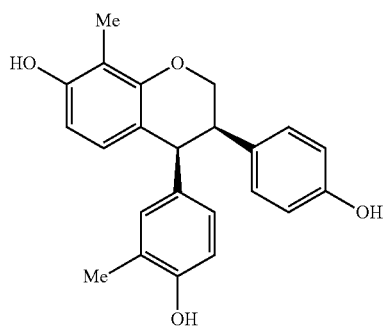 (16)

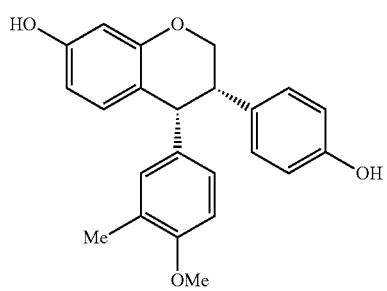 (17)

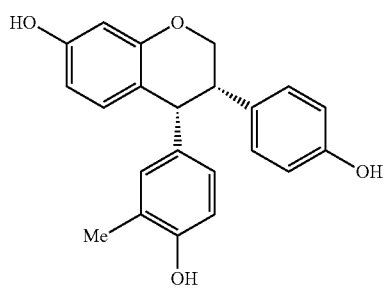 (18)

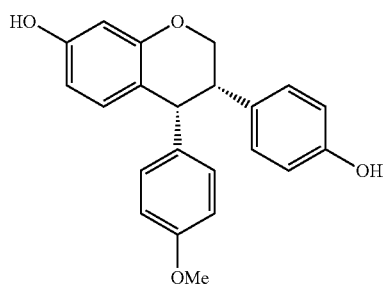 (19)

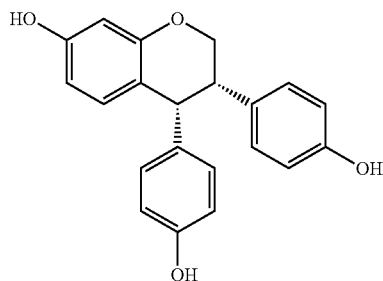 (20)

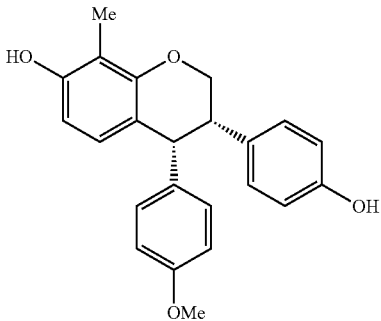 (21)

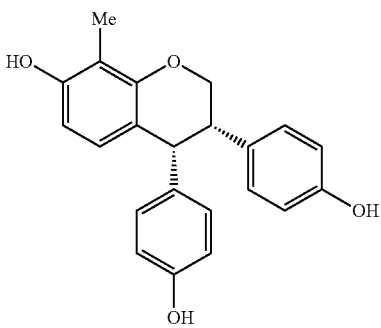 (22)

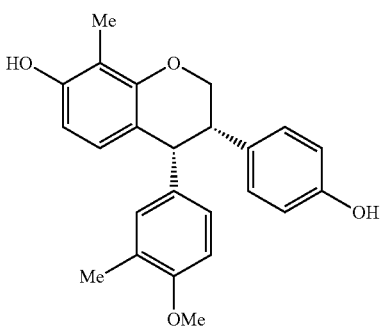 (23)

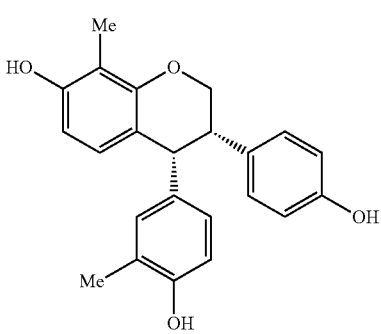 (24)

In specific embodiments, a compound of formula I or II include:

d-cis-3-(4-hydroxyphenyl)-4-(4-methoxy-3-methylphenyl)chroman-7-ol (d-1);

d-cis-3-(4-hydroxyphenyl)-4-(4-hydroxy-3-methylphenyl)chroman-7-ol (d-2);

d-cis-3-(4-hydroxyphenyl)-4-(4-methoxyphenyl)chroman-7-ol (d-3);

d-cis-3-(4-hydroxyphenyl)-4-(4-hydroxyphenyl)chroman-7-ol (d-4);

d-cis-3-(4-hydroxyphenyl)-4-(4-methoxyphenyl)-8-methyl-chroman-7-ol (d-5);

d-cis-3-(4-hydroxyphenyl)-4-(4-hydroxyphenyl)-8-methyl-chroman-7-ol (d-6);

d-cis-3-(4-hydroxyphenyl)-4-(4-methoxy-3-methylphenyl)-8-methylchroman-7-ol (d-7); and d-cis-3-(4-hydroxyphenyl)-4-(4-hydroxy-3-methylphenyl)-8-methylchroman-7-ol (d-8).

In additional or further embodiments, the compounds described herein are used in the form of pro-drugs. In additional or further embodiments, the compounds described herein are metabolized upon administration to an organism in need to produce a metabolite that is then used to produce a desired effect, including a desired therapeutic effect.

Cyclodextrin

The composition described herein comprises a cyclodextrin. In some embodiments, the cyclodextrin has a concentration (w/v) ranging from about 0.001% to about 50%. In other embodiments, the cyclodextrin has a concentration (w/v) ranging from about 2% to about 48%. In still other embodiments, the cyclodextrin has a concentration (w/v) ranging from about 4% to about 45%. In yet other embodiments, the cyclodextrin has a concentration (w/v) ranging from about 10% to about 43%. In yet other embodiments, the cyclodextrin has a concentration (w/v) ranging from about 15% to about 40%. In yet other embodiments, the cyclodextrin has a concentration (w/v) ranging from about 20% to about 38%. In yet other embodiments, the cyclodextrin has a concentration (w/v) ranging from about 22% to about 37%. In yet other embodiments, the cyclodextrin has a concentration (w/v) ranging from about 25% to about 35%. In a preferred embodiment, the cyclodextrin has a concentration (w/v) ranging from about 28% to about 32%.

Some embodiments described herein provide a composition comprising cyclodextrin, wherein the cyclodextrin has a concentration (w/v) of about 15%, 18%, 20%, 22%, 25%, 26%, 27%, 28%, 29%, 30%, 31%, 32%, 33%, 34%, 35%, 36%, 37%, or 38% when cyclodextrin derivative is SBE7-β-CD (Captisol®). In one embodiment, the cyclodextrin has a concentration (w/v) of about 30% when cyclodextrin derivative is SBE7-β-CD (Captisol®). In another embodiment, the solubility enhancer has a concentration (w/v) of about 29.4% when the cyclodextrin derivative is SBE7-β-CD (Captisol®).

Additional cyclodextrin derivatives suitable for use in intravenous compositions described herein are known in the art and are described in, e.g., U.S. Pat. Nos. 5,134,127 and 5,376,645 each of which is incorporated by reference herein for such disclosure. In addition, examples of suitable cyclodextrin derivatives are described below.

Suitable cyclodextrins and derivatives useful in certain embodiments of the compositions, methods and kits described herein include, for example, those described in Challa et al., AAPS PharmSciTech 6(2): E329-E357 (2005), U.S. Pat. Nos. 5,134,127, 5,376,645, 5,874,418, each of which is incorporated by reference herein for such disclosure. In some embodiments, suitable cyclodextrins or cyclodextrin derivatives for use in certain embodiments of the compositions, methods and kits described herein include, but are not limited to, α-cyclodextrins, β-cyclodextrins, γ-cyclodextrins, SAE-CD derivatives (e.g., SBE-α-CD, SBE-β-CD, SBE1-β-CD, SBE4-β-CD, SBE7-β-CD (Captisol®), and SBE-γ-CD) (Cydex, Inc. Lenexa, KS), hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethylhydroxypropyl ethers of α-, β- and γ-cyclodextrin; and the maltosyl, glucosyl and maltotriosyl derivatives of α-, β- and γ-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives. Specific cyclodextrin derivatives for use herein include hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, diethyl-β-cyclodextrin, glucosyl-α-cyclodextrin, glucosyl-β-cyclodextrin, diglucosyl-β-cyclodextrin, tri-O-methyl-β-cyclodextrin, tri-O-ethyl-β-cyclodextrin, tri-O-butyryl-β-cyclodextrin, tri-O-valeryl-β-cyclodextrin, and di-O-hexanoyl-β-cyclodextrin, as well as methyl-β-cyclodextrin, and mixtures thereof such as maltosyl-β-cyclodextrin/dimaltosyl-β-cyclodextrin. Any suitable procedure may be utilized for preparing such cyclodextrins including, e.g., those procedures described in U.S. Pat. No. 5,024,998, which is incorporated by reference herein for such disclosure. Other cyclodextrins suitable for use in certain embodiments of the compositions, methods and kits described herein include the carboxyalkyl thioether derivatives such as ORG 26054 and ORG 25969 by ORGANON (AKZO-NOBEL), hydroxybutenyl ether derivatives by EASTMAN, sulfoalkyl-hydroxyalkyl ether derivatives, sulfoalkyl-alkyl ether derivatives, and other derivatives, for example as described in U.S. Patent Application Nos. 2002/0128468, 2004/0106575, 2004/0109888, and 2004/0063663, or U.S. Pat. Nos. 6,610,671, 6,479,467, 6,660,804, or 6,509,323, each of which is specifically incorporated by reference herein for such disclosure.

Hydroxypropyl-β-cyclodextrin can be obtained from Research Diagnostics Inc. (Flanders, N.J.). Exemplary hydroxypropyl-β-cyclodextrin products include Encapsin® (degree of substitution ~4) and Molecusol® (degree of substitution ~8); however, embodiments including other degrees of substitution are also available and are within the scope of the present invention.

Dimethyl cyclodextrins are available from FLUKA Chemie (Buchs, CH) or Wacker (Iowa). Other derivatized cyclodextrins suitable for use in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-β-cyclodextrins, e.g., succinyl-β-cyclodextrin (SCD). All of these materials can be made according to methods known in the art and/or are available commercially. Suitable derivatized cyclodextrins are disclosed in Modified Cyclodextrins: Scaffolds and Templates for Supramolecular Chemistry (Eds. Christopher J. Easton, Stephen F. Lincoln, Imperial College Press, London, UK, 1999) and New Trends in Cyclodextrins and Derivatives (Ed. Dominique Duchene, Editions de Sante, Paris, France, 1991).

Liquid Vehicle

In some embodiments, any composition described herein comprises a compound of formula I or a compound of formula II, a cyclodextrin and further comprises a liquid vehicle. In some embodiments, the liquid vehicle is aqueous. In specific embodiments, the liquid vehicle is isotonic or hypotonic. In other embodiments, the liquid vehicle comprises a water miscible, physiologically acceptable solvent. Among the acceptable vehicles that are optionally employed by way of non-limiting example, are sterile water, Ringer's solution, phosphate buffered saline solution, U.S.P. and isotonic sodium chloride solution, ethanol, and 1,3-butanediol.

In addition, sterile, fixed oils are optionally employed as a solvent or suspending medium. For this purpose any bland fixed oil is optionally employed including synthetic mono- or diglycerides. Suitable lipophilic solvents or vehicles include fatty oils such as sesame oil, or synthetic fatty acid esters, such as ethyl oleate or triglycerides, or liposomes or other microparticulate systems may be used to target the agent to blood components or one or more organs. In some embodiments, the sterile injectable preparation is a sterile injectable oil-in-water microemulsion where the active ingredient is dissolved in the oily phase. In certain embodiments, the active ingredient is first dissolved in a mixture of soybean oil and lecithin. The oil solution then introduced into a water and glycerol mixture and processed to form a microemulsion. In further or additional embodiments, the injectable solutions or microemulsions are introduced into an individual's blood-stream by local bolus injection. Alternatively, in some embodiments, it is advantageous to administer the solution or microemulsion in such a way as to maintain a constant circulating concentration of the instant compound. In order to maintain such a constant concentration, a continuous intravenous delivery device are utilized. An example of such a device is the Deltec CADD-PLUS™ model 5400 intravenous pump.

In other embodiments, the pharmaceutical composition is in the form of a sterile injectable aqueous or oleagenous suspension for intramuscular and subcutaneous administration. In further or additional embodiments, this suspension is formulated using those suitable dispersing or wetting agents and suspending agents which have been mentioned above. In some embodiments, the sterile injectable preparation is a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose in some embodiments, any bland fixed oil is optionally employed including synthetic mono- or diglycerides. In addition, fatty acids such as oleic acid find use in the preparation of injectables.

In certain embodiments, the liquid vehicle and/or formulations are sterilized, for example, by filtration through a bacterial-retaining filter, or by incorporating sterilizing agents in the form of sterile solid compositions which is dissolved or dispersed in sterile water or other sterile medium prior to use.

Additional Excipients and/or Agents

Some embodiments provided herein describe a pharmaceutical composition, wherein the composition further comprises one or more pharmaceutical carriers, excipients, auxiliaries, binders and/or diluents.

Any composition described herein optionally comprises minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In some embodiments, the composition further comprises one or more of lactose, dextrose, mannitol, pH buffering agents, antioxidant agents, preservative agents, tonicity adjusters or a combination thereof. Examples of pharmaceutically acceptable carriers that are optionally used include, but are not limited to aqueous vehicles, nonaqueous vehicles, antimicrobial agents, local anesthetics, suspending and dispersing agents, emulsifying agents, sequestering or chelating agents and other pharmaceutically acceptable substances.

Dosage Parameters

The concentration of the active ingredient or ingredients in the solution varies depending on intended usage. In some embodiments, the composition comprises a compound of formula I or II in an amount of about 0.2-50 mg/mL. In specific embodiments, the composition comprises a compound of formula I or II in an amount of about 25-40 mg/mL. In other embodiments, the composition comprises a compound of formula I or II in an amount of about 35 mg/mL.

Administration of any composition described herein may follow any suitable dosing schedule. In certain embodiments, the composition is administered on days 1 and 8 of each 21-day cycle. In other embodiments, the composition is administered on days 1, 8, and 15 of each 28-day cycle. In some embodiments, the composition is administered once weekly or twice weekly. In other embodiments, the composition is administered three times weekly, four times weekly, five times weekly, six times weekly or seven times weekly. In some embodiments, the composition is administered once a day, twice a day, or once every two days. In some embodiments, the composition is administered once every three days, once every four days, once every five days, or once every six days. One schedule may be preferred over another in consideration of schedules with other concomitant therapy. Doses of the composition may be held or modified, e.g., due to the observation of unacceptable side effects. In various embodiments of therapies described herein, the dosing schedule is optionally repeated, e.g., in the absence of disease progression or unacceptable side effects.

Methods

In some embodiments of the present invention, provided herein is a method of inducing apoptosis in a cancer cell. In specific embodiments, the method comprises contacting the cancer cell with a composition comprising an isoflavonoid derivative of formula I or II and a cyclodextrin. In certain embodiments, the cancer cell is present in an individual. In specific embodiments, the individual is in need of cancer therapy. In certain specific embodiments, the composition is administered to the individual intravenously. In other embodiments of the present invention, a method of treating cancer with the composition comprising an isoflavonoid derivative of formula I or II and a cyclodextrin further comprises administering cancer therapy to the individual.

In some embodiments, provided herein is a method of treating cancer in an individual in need of cancer therapy. In certain embodiments, the method comprises administering to the individual the composition comprising a compound (i.e., isoflavonoid derivative) of formula I or II and a cyclodextrin. In other embodiments of the present invention, a method of treating cancer in an individual with the composition comprising an isoflavonoid derivative of formula I or II and a cyclodextrin further comprises administering cancer therapy to an individual. In certain specific embodiments, the composition is administered to the individual intravenously.

In other embodiments of the present invention, provided herein is a method of increasing, inducing, or restoring sensitivity of a cancer cell to a chemotherapeutic agent or radiation therapy. In certain embodiments, the method comprises contacting said cell with a composition comprising a compound (i.e., isoflavonoid derivative) of formula I or II and a cyclodextrin. In certain specific embodiments, a method of administering to the cell a composition comprising a compound (i.e., isoflavonoid derivative) of formula I or II and a cyclodextrin further comprises administering cancer therapy to the cell. In certain embodiments, the cancer cell is present in an individual. In specific embodiments, the individual is in need of cancer therapy. In certain specific embodiments, the composition is administered to the individual intravenously.

In other embodiments of the present invention, provided herein is a method of increasing, inducing, or restoring sensitivity to a cancer therapy in an individual. In certain embodiments, the method comprises administering to the individual a composition comprising a compound (i.e., isoflavonoid derivative) of formula I or II and a cyclodextrin. In certain specific embodiments, a method of administering to the individual a composition comprising a compound (i.e., isoflavonoid derivative) of formula I or II and a cyclodextrin further comprises administering an additional cancer therapy to an individual in need of cancer therapy. In certain specific embodiments, the composition is administered to the individual intravenously.

Any of the method described herein, in some embodiments, further comprises administering cancer therapy to the individual or patient. In certain embodiments, the cancer therapy is, by way of non-limiting example, at least one anti-cancer agent (e.g., chemotherapeutic agent), radiation therapy, or surgery. In some embodiments, a combination of (1) administration of an effective amount of a compound described herein and (2) 1 to 3 therapies selected from the group consisting of (i) administration of an effective amount of an additional anticancer agents, (ii) administration of an effective amount of hormonal therapeutic agents and (iii) non-drug therapy prevents and/or treats cancer more effectively.

An anti-cancer agent includes but is not limited to a chemotherapeutic agent, immunotherapeutic agent, a pharmaceutical agent that inhibits the action of cell growth factor and a receptor thereof and the like. Among the chemotherapeutic agents that are optionally employed, by way of non-limiting example, are cisplatin, carboplatin, paclitaxel, gemcitabine or doxorubicin. Further, non-limiting examples of chemotherapeutic agents include alkylating agents, antimetabolites, anticancer antibiotics, plant-derived anticancer agents, and the like.

Alkylating agents include but are not limited to nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and the like.

Antimetabolites include but are not limited to mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, and the like), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Anticancer antibiotics include but are not limited to actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

Plant-derived anticancer agents include but are not limited to etoposide, etoposide phosphate, vinblastine sulfate, vincristine sulfate, vindesine sulfate, teniposide, paclitaxel, docetaxel, vinorelbine, and the like.

Immunotherapeutic agents include but are not limited to picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

Non-limiting examples of a cell growth factor in pharmaceutical agents that inhibit the action of cell growth factors or cell growth factor receptors include any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin, and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

Cell growth factor receptors include but are not limited to any receptors capable of binding to the aforementioned cell growth factors, including EGF receptor, heregulin receptor (HER2), insulin receptor, IGF receptor, FGF receptor-1 or FGF receptor-2, and the like.

Pharmaceutical agent that inhibits the action of cell growth factor include but are not limited to HER2 antibody (e.g., trastuzumab), imatinib mesylate, ZD1839 or EGFR antibody (e.g., cetuximab), antibody to VEGF (e.g., bevacizumab), VEGFR antibody, VEGFR inhibitor, and EGFR inhibitor (e.g., erlotinib).

In addition to the aforementioned drugs, other anti-cancer agents include but are not limited to L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitors (e.g., thalidomide, SU11248, and the like), α-blockers (e.g., tamsulosin hydrochloride, naftopidil, urapidil, alfuzosin, terazosin, prazosin, silodosin, and the like) serine/threonine kinase inhibitor, endothelin receptor antagonist (e.g., atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like.

Non-limiting examples of hormonal therapeutic agents include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down-regulator (e.g., fulvestrant and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiolsulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocorticohormone drugs (e.g., dexamethasone, prednisolone, betamethasone, triamcinolone, and the like), androgen synthesis inhibitors (e.g., abiraterone, and the like), and retinoid and drugs that retard retinoid metabolism (e.g., liarozole, and the like), etc. and LH-RH agonists (e.g., goserelin acetate, buserelin, leuprorelin).

The non-drug therapy is exemplified by surgery, radiotherapy, gene therapy, thermotherapy, cryotherapy, laser cauterization, and the like, and any combinations thereof.

When a composition described herein (i.e., isoflavonoid derivative of formula I or II and cyclodextrin) and a concomitant drug are used in combination, the administration time of the composition and the concomitant drug is not restricted. In some embodiments, the composition and the concomitant drug are administered to an individual simultaneously. In other embodiments, the composition and the concomitant drug are administered at staggered times.

In some embodiments, the cancer or cancer cell has lost sensitivity to a chemotherapeutic agent, anti-cancer agent or radiation therapy. In other embodiments, the combination of a composition comprising a compound of formula I or II, cyclodextrin and a chemotherapeutic agent, anti-cancer agent or radiation therapy has an enhanced effect. In some embodiments, the compositions described herein chemosensitize cancer cells, wherein the compositions lower the amount of anti-cancer agent that is required to kill the cancer cell. In other embodiments, the compositions described herein chemosensitize cancer cells, wherein the compositions convert cancer cells from a state of chemo-resistant to chemo-sensitive. In further or additional embodiments, the compositions described herein radiosensitize cancer cells, wherein compositions lower the amount of gamma-irradiation that is required to kill the cancer cell. In other embodiments, the compositions described herein radiosensitize cancer cells, wherein the compositions convert cancer cells from a state of radio-resistant to radio-sensitive.

In some embodiments, the cancer is selected from the group consisting of bladder cancer, breast cancer, metastatic breast cancer, metastatic HER2-negative breast cancer, colon cancer, rectal cancer, metastatic colorectal cancer, endometrial cancer, cervical cancer, uterine cancer, ovarian cancer, kidney cancer, liver cancer, leukemia, lung cancer (both small cell and non-small cell), squamous non-small cell lung cancer, non-squamous non-small cell lung cancer, melanoma, non-Hodgkin lymphoma, pancreatic cancer, testicular cancer, prostate cancer, thyroid cancer, sarcoma (including osteosarcoma), esophageal cancer, gastric cancer, head and neck cancer, lung cancer melanoma, myeloma, neuroblastoma, glioblastoma, and cancers of the brain. In some embodiments, the cancer is selected from, by way of non-limiting example, human breast, prostate, ovarian, pancreatic, or cervical cancer. In certain specific embodiments, the cancer is human breast cancer or ovarian cancer.

In various embodiments, any method described herein comprises administering to the cancer cell or the individual any composition or combination described herein.

Kits

In various embodiments, any composition described herein is maintained under inert atmosphere and is transferred to suitable containers, e.g. by a cannular system also under the inert atmosphere. Solvents other than water, when required, and other reagents may be chosen from medical grade reagents and solvents well known in the art. Intravenous formulations according to the invention may be packaged in containers. Containers may be chosen which are made of material. Glass containers may be used although it is preferred to use plastic containers, e.g. plastic infusion bags. In one embodiment, there is provided a single dosage form suitable for intravenous administration comprising an effective amount of the isoflavonoid compound and a cyclodextrin, such as e.g., SBE7-β-CD, and, optionally, further excipients commonly used in pharmaceutical compositions as e.g. described hereinabove.

In some embodiments, a liquid formulation of the composition is provided in a kit. In certain embodiments, the kit comprises a first pharmaceutical composition comprising an isoflavonoid compound of formula I or II and a second pharmaceutical composition comprising a cyclodextrin. The first and second formulations are optionally mixed and formulated as a liquid dosage form prior to administration to a subject. Either one or both of the first and second pharmaceutical compositions can comprise additional pharmaceutical excipients and/or additional therapeutic agents.

EXAMPLES

Example 1

Intravenous Composition of Compound d-4

Compound d-4 is dissolved in an 8% solution of Captisol® in water, at a rate of 10 mg/mL, well below its solubility limit of 27.9 mg/mL at 25° C. (20% Captisol®). Formulation is carried out under aseptic conditions. Sterility is achieved by terminal filtration through a 0.22 micron filter.

Example 2

Intravenous Composition of Compound 12

An exemplary formulation according to the invention is made according to the following general procedure. SBE7-β-CD is dissolved in water to form a solution containing about 30% w/v of cyclodextrin. Compound 12 is added to the SBE7-β-CD containing solution until a concentration of about 35 mg/mL compound 12 is reached. A formulation evaluated in animal and human clinical studies and comprising the following components in the amounts indicated is prepared as indicated above. The pH of the solution is not adjusted and no antioxidants or preservatives are included.

Example 3

Intravenous Composition of Compound 12

SBE7-β-CD is dissolved in water to form a solution containing about 30% w/v of SBE7-β-CD. Disodium ethylenediaminetetraacetate is added to the SBE7-β-CD solution at 0.01% w/v and dissolved. Compound 12 is added to the SBE7-β-CD containing solution with stirring until a concentration of about 35 mg/mL compound 12 is reached. The pH is adjusted to 7-8.5 with sodium hydroxide. The solution is purged with nitrogen gas then filtered through a 0.22 micron pore size filter prior to administration.

Example 4

Intravenous Composition of Compound 12

SBE7-β-CD is dissolved in water to form a solution containing about 30% w/v of SBE7-β-CD. Compound 12 is then added to the SBE7-β-CD containing solution with stirring until a concentration of about 35 mg/mL compound 12 is reached. The solution is purged with nitrogen gas then filtered through a 0.22 micron pore size filter. The solution is lyophilized to generate a solid formulation. Prior to use as a solution, sufficient sterile isotonic water for injection is added to the solid formulation to generate a final solution containing compound 12 35 mg/mL.

Example 5

Treatment for Breast Cancer

Human Clinical Trial of the Safety and/or Efficacy of Isoflavonoid for Breast Cancer Therapy Objective: To compare the safety and pharmacokinetics of administered composition comprising compound 12 and cyclodextrin.

Study Design: This study will be a Phase I, single-center, open-label, randomized dose escalation study followed by a Phase II study in breast cancer patients. Patients should not have had exposure to compound 12 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 12 on days 1, 8, and 15 of each 28-day cycle. Doses of compound 12 may be held or modified for toxicity based on assessments as outlined below. Treatment repeats every 28 days in the absence of unacceptable toxicity. Cohorts of 3-6 patients receive escalating doses of compound 12 until the maximum tolerated dose (MTD) for compound 12 is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 12 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 12. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 6

Treatment for Ovarian Cancer

Human Clinical Trial of the Safety and/or Efficacy of Isoflavonoid for Ovarian Cancer Therapy Objective: To compare the safety and pharmacokinetics of administered composition comprising compound 12 and cyclodextrin.

Study Design: This study will be a Phase I, single-center, open-label, randomized dose escalation study followed by a Phase II study in ovarian cancer patients. Patients should not have had exposure to compound 12 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 12 on days 1, 8, and 15 of each 28-day cycle. Doses of compound 12 may be held or modified for toxicity based on assessments as outlined below. Treatment repeats every 28 days in the absence of unacceptable toxicity. Cohorts of 3-6 patients receive escalating doses of compound 12 until the maximum tolerated dose (MTD) for compound 12 is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 12 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 12. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 7

Intravenous Composition

An exemplary formulation according to the invention is made according to the following general procedure. SBE7-β-CD is dissolved in water to form a solution containing about 30% w/v of cyclodextrin. Any one of the compounds 1-24 is added to the SBE7-β-CD containing solution until a concentration of about 35 mg/mL the compound is reached. A formulation evaluated in animal and human clinical studies and comprising the following components in the amounts indicated is prepared as indicated above. The pH of the solution is not adjusted and no antioxidants or preservatives are included.

Example 8

Intravenous Composition

SBE7-β-CD is dissolved in water to form a solution containing about 30% w/v of SBE7-β-CD. Disodium ethylenediaminetetraacetate is added to the SBE7-β-CD solution at 0.01% w/v and dissolved. Any one of the compounds 1-24 is then added to the SBE7-β-CD containing solution with stirring until a concentration of about 35 mg/mL compound is reached. The pH is adjusted to 7-8.5 with sodium hydroxide. The solution is purged with nitrogen gas then filtered through a 0.22 micron pore size filter prior to administration.

Example 9

Intravenous Composition

SBE7-β-CD is dissolved in water to form a solution containing about 30% w/v of SBE7-β-CD. Any one of the compounds 1-24 is then added to the SBE7-β-CD containing solution with stirring until a concentration of about 35 mg/mL compound is reached. The solution is purged with nitrogen gas then filtered through a 0.22 micron pore size filter. The solution is lyophilized to generate a solid formulation. Prior to use as a solution, sufficient sterile isotonic water for injection is added to the solid formulation to generate a final solution containing 35 mg/mL of compound.

Example 10

Treatment for Breast Cancer

Human Clinical Trial of the Safety and/or Efficacy of Isoflavonoid for Breast Cancer Therapy Objective: To compare the safety and pharmacokinetics of administered composition comprising any one of the compounds 1-24 and a cyclodextrin.

Study Design: This study will be a Phase I, single-center, open-label, randomized dose escalation study followed by a Phase II study in breast cancer patients. Patients should not have had exposure to the compound prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. any one of compound 1-24 on days 1, 8, and 15 of each 28-day cycle. Doses of the compound may be held or modified for toxicity based on assessments as outlined below. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive any one of the compounds 1-24 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of the compound. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 11

Treatment for Ovarian Cancer

Human Clinical Trial of the Safety and/or Efficacy of Isoflavonoid for Ovarian Cancer Therapy Objective: To compare the safety and pharmacokinetics of administered composition comprising any one of the compounds 1-24 and a cyclodextrin.

Study Design: This study will be a Phase I, single-center, open-label, randomized dose escalation study followed by a Phase II study in ovarian cancer patients. Patients should not have had exposure to the compound prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. any one of compounds 1-24 on days 1, 8, and 15 of each 28-day cycle. Doses of the compound may be held or modified for toxicity based on assessments as outlined below. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive any one of the compounds 1-24 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of the compound. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

What is claimed is:

1. A pharmaceutical composition comprising i) d-cis-3-(4-hydroxyphenyl)-4-(4-hydroxyphenyl)-8-methylchroman-7-ol; and ii) about 28 to about 32% w/v SBE7-β-CD.

2. The composition of claim 1, wherein the composition comprises about 30% w/v SBE7-β-CD.

3. The composition of claim 1, wherein the composition further comprises water.

4. The composition of claim 1, wherein the composition comprises d-cis-3-(4-hydroxyphenyl)-4-(4-hydroxyphenyl)-8-methylchroman-7 -ol in an amount of about 35 mg/mL.

5. The composition of claim 1, wherein the composition further comprises a chemotherapeutic agent selected from the group consisting of cisplatin, carboplatin, paclitaxel, gemcitabine or doxorubicin.

6. A method of treating cancer in an individual in need of cancer therapy, the method comprising administering to the individual a composition comprising i) d-cis-3-(4-hydroxyphenyl)-4-(4-hydroxyphenyl)-8-methylchroman-7-ol; and ii) about 28 to about 32% w/v SBE7-β-CD.

7. The method of claim 6, wherein the composition increases or induces sensitivity of the cancer to a chemotherapeutic agent, anti-cancer agent, or radiation therapy.

8. The method of claim 7, wherein the cancer had lost sensitivity to a chemotherapeutic agent, anti-cancer agent, or radiation therapy.

9. The method of claim 6, wherein said cancer is selected from the group consisting of bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer, and cancers of the brain.

10. The method of claim 6, wherein said cancer is human breast cancer or ovarian cancer.

11. A kit comprising a sealable, plastic infusion bag; and a composition comprising i) d-cis-3-(4-hydroxyphenyl)-4-(4-hydroxyphenyl)-8-methylchroman-7-ol; and ii) about 28 to about 32% w/v SBE7-β-CD.

* * * * *